United States Patent [19]
Lingenhöle

[11] 3,952,416
[45] Apr. 27, 1976

[54] DENTAL HANDPIECE
[75] Inventor: Bernhard Lingenhöle, Biberbach, Germany
[73] Assignee: Kaltenbach & Voigt, Biberach an der Riss, Germany
[22] Filed: Dec. 9, 1974
[21] Appl. No.: 531,191

[30] Foreign Application Priority Data
Dec. 7, 1973  Germany............... 7343581[U]

[52] U.S. Cl. .................................................. 32/27
[51] Int. Cl.² ......................................... A61C 1/10
[58] Field of Search ............ 32/26, 27, 28; 415/503

[56] References Cited
UNITED STATES PATENTS
3,175,293   3/1965   Borden ..................... 415/503 X FOREIGN PATENTS OR APPLICATIONS
1,246,573   9/1971   United Kingdom ............... 32/27
1,098,162   1/1961   Germany ........................ 32/27

Primary Examiner—Louis G. Mancene
Assistant Examiner—Jack Q. Lever
Attorney, Agent, or Firm—Haseltine, Lake & Waters

[57] ABSTRACT

A dental handpiece which includes a head and a holding sleeve associated therewith. The holding sleeve incorporates therein gaseous and liquid coolant lines each of which is in communication with a mixing line in turn in communication with one or more discharge nozzles for discharging an air-water coolant spray. Each of the gaseous and liquid coolant lines is provided with throttle means which serves to reduce the effective cross-sectional areas thereof.

5 Claims, 1 Drawing Figure

U.S. Patent   April 27, 1976   3,952,416
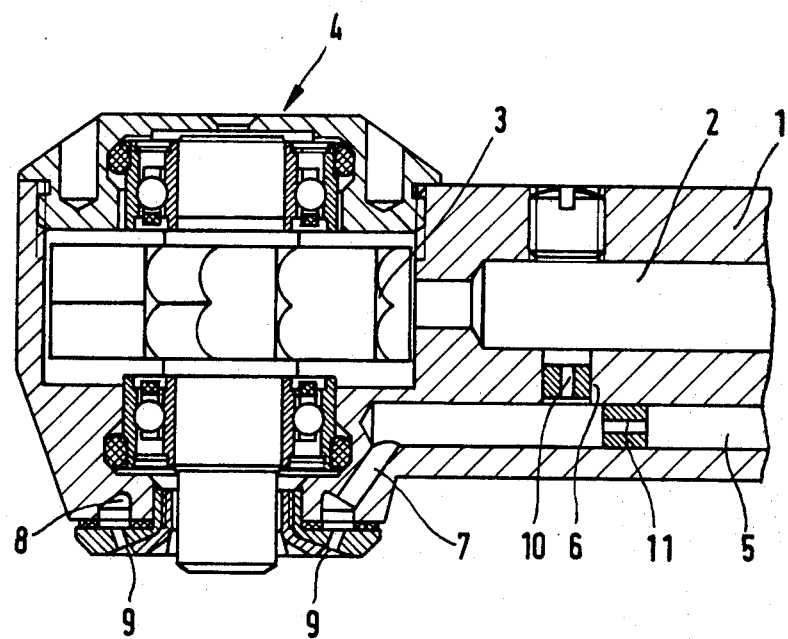

DENTAL HANDPIECE

The present invention relates to a dental handpiece and more particularly to such a handpiece which is provided with gaseous and liquid coolant lines which are in communication with nozzle means adapted to discharge a cooling spray of gas and liquid.

BACKGROUND OF THE INVENTION

It has been known heretofore to provide a dental handpiece with a coolant under pressure such as air and/or water. German Auslegeschrift No. 1,098,162 for example, discloses a dental handpiece of this character wherein a cooling air line is fed by the exhaust air of a pressure air turbine mounted within the head thereof.

Generally, handpieces of the type described are subjected to the action of the coolant medium, such as air and/or water, under a predetermined pressure. On occasion the pressure in the coolant air line and/or in the cooling water line may fluctuate. The cause of this may, for example, be due to a decrease in the propelling air pressure and this may result in the decrease in cooling air pressure. This may occur due to a defect in the compressor installation or, alternatively, due to the intentional adjustment of the propelling air quantity in connection with regulation of the turbine speed. If, as a consequence thereof, the pressure in the cooling air line falls below that in the cooling water line, the water being introduced via the cooling water line may be displaced into the cooling air line with the result that this water may cause damage to the rotating turbine or to the compressor installation. Also, the desired spray of air and water from the outlet nozzle, may be interrupted or otherwise affected. The resultant effluent may simply be a discharge of water at a reduced pressure.

It will thus be seen that one of the problems existent with dental handpieces currently available has been in insuring the maintenance of the desired spray of air and water from the outlet nozzle or nozzles despite fluctuations in pressure in the air and/or water lines. It has also been a problem in devising the arrangement of gaseous and liquid coolant lines such that the liquid, i.e. water, is prevented from entering the gaseous coolant, i.e., air line or vice versa since these appear to be common causes of impairment of the flow of air and water from the discharge nozzles.

SUMMARY OF THE INVENTION

It is, therefore, one object of this invention to provide a dental handpiece having gaseous and liquid coolant lines and one or more discharge nozzles with an arrangement of throttle means which prevents the flow of gaseous coolant into the liquid coolant line and vice versa when fluctuations in the pressure in either line develops.

It is another object of this invention to provide a dental handpiece of the character described wherein air and water cooling lines are so constructed and arranged in relation to each other and to a mixing line that the flow of the desired spray of an air-water mixture from one or more discharge nozzles is assured.

These and other objects and advantages of the invention will become readily apparent to persons skilled in the art from the following description.

According to the present invention there is provided a dental handpiece including a head and a holding sleeve associated therewith having at least one coolant line therein, said head having discharge nozzle means for the discharge of a coolant spray, said handpiece comprising separate gaseous and liquid coolant lines in said holding sleeve in communication with each other, a mixing line positioned downstream of the point of communication between said gaseous and liquid coolant lines adapted to receive gaseous and liquid coolant from said respective lines and to admix same, said discharge nozzle means being in fluid communication with said mixing line and having a smaller effective cross-sectional area than that of said mixing line, and throttle means being positioned in each of said gaseous and liquid coolant lines, the sum of the cross-sectional areas of both of said throttle means being not greater than the effective cross-sectional area of said discharge nozzle means.

BRIEF DESCRIPTION OF THE DRAWING

In order that the invention may be more fully understood it will now be described, by way of example, with reference to the accompanying drawing which is a sectional view of the head of an angled dental handpiece and which incorporates the features of the invention.

DETAILED DESCRIPTION OF THE INVENTION

Referring now to the drawing, there is shown a dental handpiece having a holding or grasping sleeve 1 which incorporates a propellant air line 2 therein. The handpiece is given head 4 which houses a turbine having an impeller 3 drivable when subjected to the action of pressure air. Furthermore, the sleeve 1 incorporates a liquid coolant line in the form of a cooling water line 5. Also, the sleeve 1 incorporates a gas coolant line in the form of a cooling air line 6 which is in communication with the line 2 upstream of the impeller 3 and which exits into the cooling water line 5. Downstream of the merging of the lines 5 and 6, is arranged a mixing line 7 which provides communication between an end of the merging or common line for air and water from lines 6 and 5 respectively, to an annular distributor or manifold duct 8. The distributor duct 8 is provided with outlet nozzle means in the form of outwardly directed outflow nozzles 9 for discharging a cooling spray of air-water mixture. This air-water mixture formed into a spray is obtained in view of the fact that the outlet nozzles 9 have a smaller cross-sectional area relative to that of the mixing line 7 or the distributor duct 8.

While there has been illustrated outlet nozzle means in the form of a plurality of nozzles 9, it is to be understood that the nozzle means may be constituted by one or more nozzles as desired.

In order to prevent flow-back of water medium through air line 6, or air medium through water line 5, each of the lines 6 and 5 is provided with a respective throttle means 10 or 11. As shown, the throttle means comprises a passageway of reduced cross-sectional area positioned in each of the lines. The sum of the cross-sectional areas of the two throttle means 10, 11 is equal to or less than the cross-sectional area of the nozzle means i.e. of the one or more outlet nozzles 9. As shown, the cross-sectional area of the throttle means 11 is smaller than that of the throttle means 10.

If desired, each of the throttle means 10, 11 may be arranged so as to permit variation, as desired, in its cross-sectional area. This may be advantageous in connection with the initial setting-up of the dental handpiece in order to adapt it for use with particular operating pressures of air and water which may be available.

Conveniently, the dental handpiece is adapted to operate with compressed air as the gaseous medium and with water as the liquid medium. In such event, a dental handpiece according to the invention may be operated in such a manner that a spray of the desired air-water mixture can flow out of the outlet nozzle means, and water can be prevented from entering the air line, or air can be prevented from entering the water line, since also in the latter case the outflow of the desired air-water mixture would be impaired.

By the arrangement of the two the two throttle means (one in the air line and one in the water line), in the event of a pressure drop in the air line or in the water line, the other medium in each particular instance is prevented from flowing into the line affected by the pressure drop. There is the advantage that the medium of the line affected by the pressure drop continues to flow through the throttle means of that line and, as desired, flows to the mixing line and, from there, flows mixed with the other medium as air-water mixture out of the outlet nozzle means.

Preferably, the outlet nozzle means comprises a plurality of outlet nozzles which communicate with a distributor or manifold duct which, in turn, is in communication with the mixing line.

If desired, each throttle means may be provided with a variation in its cross-sectional area. In such event, the throttle means may be adapted to pressures which, possibly, vary from the outset, in the cooling air line and in the cooling water line.

I claim:

1. A dental handpiece including a head and a holding sleeve associated therewith having at least one coolant line therein, said head having discharge nozzle means for the discharge of a coolant spray, said handpiece having separate gaseous and liquid coolant lines in said holding sleeve in communication with each other, a mixing line positioned downstream of the point of communication between said gaseous and liquid coolant lines adapted to receive gaseous and liquid coolant from said respective lines and to admix same, said discharge nozzle means being in fluid communication with said mixing line and having a smaller effective cross-sectional area than that of said mixing line, and throttle means being positioned in each of said gaseous and liquid coolant lines, the sum of the cross-sectional areas of both of said throttle means being not greater than the effective cross-sectional area of said discharge nozzle means.

2. A dental handpiece according to claim 1, wherein an annular distributor duct is provided intermediate said mixing line and discharge nozzle means, a plurality of discharge nozzles being arranged so as to receive a mixture of gaseous and liquid coolant for discharge therefrom.

3. A dental handpiece according to claim 1, wherein each of said throttle means comprises a passageway of reduced cross-sectional area positioned in said gaseous and liquid coolant lines.

4. A dental handpiece according to claim 3, wherein each of said passageways has a uniform cross-sectional area.

5. A dental handpiece according to claim 1, wherein said gaseous coolant line is connected with a source of pressurized air and said liquid coolant line is connected to a source of water under pressure.

* * * * *